(12) United States Patent
Takigawa et al.

(10) Patent No.: US 9,007,578 B2
(45) Date of Patent: Apr. 14, 2015

(54) METHOD FOR MEASUREMENT OF PROPERTIES OF ANALYTE

(75) Inventors: Kazuhiro Takigawa, Nagaokakyo (JP); Takashi Kondo, Nagaokakyo (JP); Seiji Kamba, Nagaokakyo (JP); Yuichi Ogawa, Sendai (JP)

(73) Assignees: Murata Manufacturing Co., Ltd., Nagaokakyo-Shi, Kyoto-Fu (JP); National University Corporation Tohoku University, Sendai-Shi, Miyagi (JP)

(*) Notice: Subject to any disclaimer, the term of this patent is extended or adjusted under 35 U.S.C. 154(b) by 485 days.

(21) Appl. No.: 13/398,016

(22) Filed: Feb. 16, 2012

(65) Prior Publication Data

US 2012/0137755 A1  Jun. 7, 2012

Related U.S. Application Data (63) Continuation of application No. PCT/JP2010/062214, filed on Jul. 21, 2010.

(30) Foreign Application Priority Data

Aug. 21, 2009  (JP) ................................ 2009-192329

(51) Int. Cl.
  *G01N 21/25* (2006.01)
  *G01N 21/3581* (2014.01)

(52) U.S. Cl.
  CPC ................................. *G01N 21/3581* (2013.01)

(58) Field of Classification Search
  CPC . G01N 21/3581; G01N 21/25; G01N 21/251; G01N 21/4788; G01N 33/54373
  USPC .................................................. 356/305, 328
  See application file for complete search history.

(56) References Cited

U.S. PATENT DOCUMENTS

| 7,399,445 | B2 * | 7/2008 | Kuroda et al. ................ 422/504 |
| 7,435,385 | B2 * | 10/2008 | Lin et al. .................... 422/82.05 |
| 2003/0132392 | A1 * | 7/2003 | Kuroda et al. ................ 250/397 |
| 2004/0132172 | A1 * | 7/2004 | Cunningham et al. ..... 435/287.2 |
| 2008/0218734 | A1 | 9/2008 | Higashi et al. |
| 2010/0025586 | A1 | 2/2010 | Ogawa et al. |

FOREIGN PATENT DOCUMENTS

| JP | 2007-163170 A | 6/2007 |
| JP | 2008-185552 A | 8/2008 |
| JP | 2008-224240 A | 9/2008 |

OTHER PUBLICATIONS

Hisa Yoshida et al., "Label-free Detection of Protein Using a Metallic Mesh" IEICE Tech0nical Report, vol. 107, No. 355, Nov. 20, 2007, pp. 99-102.

* cited by examiner

*Primary Examiner* — Peter Macchiarolo
*Assistant Examiner* — Nathaniel Kolb
(74) *Attorney, Agent, or Firm* — Arent Fox LLP (57) ABSTRACT

A measurement method that includes irradiating a void-arranged structure on which an analyte has been held with an electromagnetic wave, detecting an electromagnetic wave scattered on the void-arranged structure, and determining a property of the analyte on the basis of at least one parameter, the parameter including the amount of change in the ratio of the detected electromagnetic wave to the irradiated electromagnetic wave at a specific frequency between the presence and the absence of the analyte.

8 Claims, 7 Drawing Sheets

METHOD FOR MEASUREMENT OF PROPERTIES OF ANALYTE

CROSS REFERENCE TO RELATED APPLICATIONS

The present application is a continuation of International application No. PCT/JP2010/062214, filed Jul. 21, 2010, which claims priority to Japanese Patent Application No. 2009-192329, filed Aug. 21, 2009, the entire contents of each of which are incorporated herein by reference.

FIELD OF THE INVENTION

The present invention relates to a method for measuring properties of an analyte by holding the analyte on a void-arranged structure, applying an electromagnetic wave to the void-arranged structure holding the analyte and analyzing a scattered spectrum thereof in order to analyze properties of a substance.

BACKGROUND OF THE INVENTION

In general, a method for measuring properties of an analyte by holding the analyte on a void-arranged structure, applying an electromagnetic wave to the void-arranged structure holding the analyte and analyzing a transmittance spectrum thereof is employed in order to analyze properties of a substance. More specifically, a technique of analyzing a transmittance spectrum by applying a terahertz wave to a metal mesh filter to which protein or the like employed as an analyte adheres can be cited, for example.

As the prior art of such a technique of analyzing a transmittance spectrum with an electromagnetic wave, Japanese Patent Laying-Open No. 2008-185552 (Patent Literature 1) discloses a method constituted of a void-arranged structure (more specifically, a meshy conductor plate) having a void region, an analyte held on the surface of the void-arranged structure, an electromagnetic wave application portion applying an electromagnetic wave toward the analyte and an electromagnetic wave detection portion measuring the electromagnetic wave transmitted through the void-arranged structure for measuring properties of the analyte on the basis of that the electromagnetic wave projected from the electromagnetic application portion toward the void-arranged structure is inclined incident upon a plane including the void region and the position of a dip waveform caused in a frequency characteristic of a measured value moves due to the presence of the analyte (FIGS. 3 and 9 of Japanese Patent Laying-Open No. 2008-185552).

In a measurement method for determining the analyte from a quantity of change (quantity of shifting of a reverse peak) in a frequency corresponding to the minimum of the dip waveform in a transmittance spectrum obtained from the aforementioned transmittance at a time of changing the frequency of the aforementioned electromagnetic wave as applied in a constant range, however, it has been difficult to determine an analyte of a small quantity (particularly not more than about 100 ng/mm$^2$) since the quantity of shifting of the reverse peak reduces and becomes smaller than the detection limit (frequency resolution) (refer to FIG. 9 of Japanese Patent Laying-Open No. 2008-185552). Further, such a method requires a mechanism for acquiring information of the frequency, and hence a measuring apparatus such as a spectrometer, for example, large-sized and hard to control is required.

PTL 1: Japanese Patent Laying-Open No. 2008-185552

SUMMARY OF THE INVENTION

In consideration of the aforementioned circumstances, an object of the present invention is to provide a method for measurement of properties of an analyte, which is improved in measuring sensitivity and capable of measuring an analyte of a smaller quantity. Another object of the present invention is to provide a method for simply measuring properties of an analyte.

The present invention provides a measurement method including the steps of:

holding an analyte on a void-arranged structure, applying an electromagnetic wave to the aforementioned void-arranged structure holding the aforementioned analyte, and detecting the electromagnetic wave scattered by the aforementioned void-arranged structure, for measuring properties of the aforementioned analyte on the basis of at least one parameter, characterized in that the aforementioned parameter includes a quantity of change, resulting from the presence of the analyte, in the ratio of the detected electromagnetic wave to the applied electromagnetic wave at a specific frequency.

Preferably, the aforementioned specific frequency is a frequency other than a minimum point of a dip waveform, or a frequency other than a maximum point of a peak waveform.

Preferably, the aforementioned specific frequency is a frequency other than a minimum point of a dip waveform in a frequency characteristic of transmittance of the electromagnetic wave transmitted through the aforementioned void-arranged structure (1), or a frequency other than a maximum point of a peak waveform in a frequency characteristic of reflectance of the electromagnetic wave reflected by the aforementioned void-arranged structure (1).

Preferably, the aforementioned specific frequency is a frequency in the aforementioned dip waveform or in the aforementioned peak waveform.

Preferably, the aforementioned specific frequency is a frequency outside a full width at half maximum (FWHM) in the aforementioned dip waveform or in the aforementioned peak waveform.

Preferably, the aforementioned specific frequency is a frequency other than the aforementioned dip waveform or a frequency other than the aforementioned peak waveform, and the ratio of the detected electromagnetic wave to the applied electromagnetic wave at the aforementioned specific frequency is a ratio in a frequency characteristic of a portion adjacent to the aforementioned dip waveform wherein the ratio of the detected electromagnetic wave to the applied electromagnetic wave is higher than that on both ends of a full width at half maximum (FWHM) of the dip waveform, or in a frequency characteristic of a portion adjacent to the aforementioned peak waveform wherein the ratio of the detected electromagnetic wave to the applied electromagnetic wave is lower than that on both ends of a full width at half maximum (FWHM) of the peak waveform.

Preferably, the aforementioned parameter includes a quantity of change, resulting from the presence of the analyte, in the width of the aforementioned dip waveform or the aforementioned peak waveform.

Preferably, the aforementioned void-arranged structure is a structure causing a pseudo-TE11 mode resonance phenomenon. Preferably, the aforementioned void-arranged structure is a structure reducing a pseudo-TE10 mode resonance phenomenon.

In the present invention, properties of an analyte are measured with a parameter of a quantity of change, resulting from the presence of the analyte, in transmittance at a time of applying an electromagnetic wave of a specific frequency to a void-arranged structure holding the analyte, whereby measuring sensitivity improves, and that it becomes possible to measure an analyte of a smaller quantity.

DETAILED DESCRIPTION OF THE PREFERRED EMBODIMENTS

Figure 1:
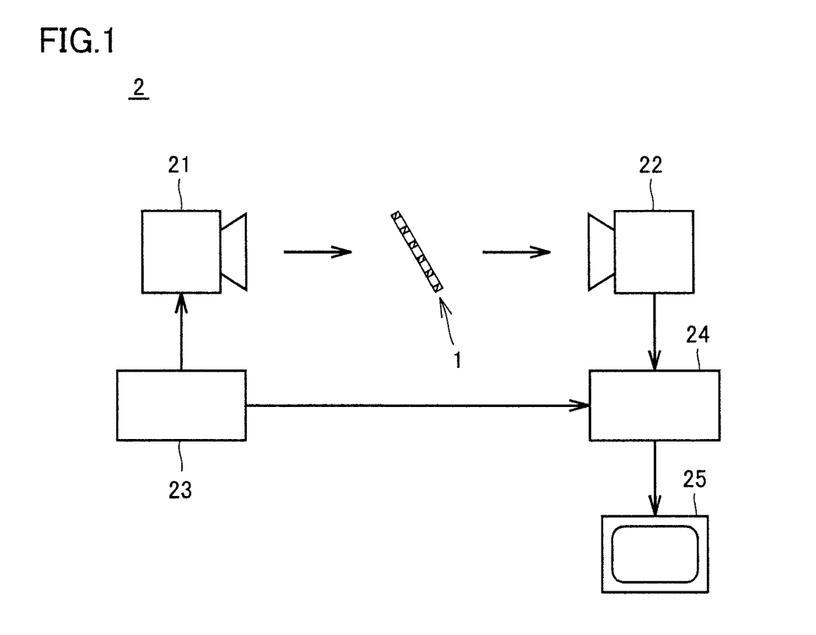
FIG. 1 is a schematic diagram for illustrating a measurement method according to the present invention.

An example of a measurement method according to the present invention is described with reference to FIG. 1. FIG. 1 is a diagram schematically showing the overall structure of a measuring apparatus 2 according to the present invention and arrangement of a void-arranged structure 1 in measuring apparatus 2. As shown in FIG. 1, this measuring apparatus 2 includes an application portion 21 generating and applying an electromagnetic wave and a detection portion 22 detecting the electromagnetic wave transmitted through void-arranged structure 1. Measuring apparatus 2 further includes an application control portion 23 controlling operation of application portion 21, an analytical treatment portion 24 analyzing a detection result of detection portion 22 and a display portion 25 displaying an analytical result of analytical treatment portion 24. Application control portion 23 may be connected also to analytical treatment portion 24, in order to synchronize timings of detection.

While FIG. 1 shows a case where scattering is transmission, i.e., a case of measuring transmittance of the electromagnetic wave, "scattering" denotes a wide-ranging concept including transmission which is one mode of forward scattering, reflection which is one mode of backward scattering and the like in the present invention, and is preferably transmission or reflection. More preferably, scattering is transmission in a zero-order direction or reflection in the zero-order direction.

Assuming that $d$ represents a grating space of a diffraction grating (space between void portions in this specification), $i$ represents an angle of incidence, $\theta$ represents an angle of diffraction and $\lambda$ represents a wavelength in general, a spectrum diffracted by the diffraction grating can be expressed as:

$$d(\sin i - \sin \theta) = n\lambda \quad (1)$$

The zero-order in the aforementioned "zero-order direction" indicates a case where $n$ in the above formula (1) is zero. $d$ and $\lambda$ cannot become zero, and hence n=0 holds only in a case of $\sin i - \sin \theta = 0$. Therefore, the aforementioned "zero-order direction" denotes a time when the angle of incidence and the angle of diffraction are equal to each other, i.e., a direction in which the traveling direction of the electromagnetic wave remains unchanged.

In aforementioned measuring apparatus 2, application portion 21 generates·radiates the electromagnetic wave under the control of application control portion 23. The electromagnetic wave radiated from application portion 21 is applied to void-arranged structure 1, and the electromagnetic wave transmitted through void-arranged structure 1 is detected by detection portion 22. The electromagnetic wave detected by detection portion 22 is transferred to analytical treatment portion 24 as an electric signal, and displayed on display portion 25 in a format visually recognizable as a frequency characteristic of transmittance (transmittance spectrum).

While such an electromagnetic wave employed in the measurement method according to the present invention is not particularly restricted so far as the same is an electromagnetic wave capable of causing scattering in response to the structure of the void-arranged structure but any of a radio wave, an infrared ray, a visible ray, an ultraviolet ray, an X-ray, a gamma ray and the like can be used and the frequency thereof is not particularly restricted either, the same is a terahertz wave having a frequency of preferably 1 GHz to 1 PHz, and more preferably 20 GHz to 120 THz. Further, the electromagnetic wave is preferably an electromagnetic wave of linear polarization. As a specific electromagnetic wave, a terahertz wave generated by an optical rectification effect of an electrooptic crystal such as ZnTe with a light source of a short-beam pulse laser, an infrared ray radiated from a high-pressure mercury lamp or a ceramic lamp, a visible ray emitted from a semiconductor laser or an electromagnetic wave radiated from an optical conduction antenna can be cited, for example.

In the present invention, measurement of properties of an analyte indicates an operation of performing determination of a compound employed as the analyte and various qualifications of a dielectric constant and the like, and a case of measuring the content of an analyte of a small quantity in a solution or the like or a case of performing identification of an analyte can be cited, for example. More specifically, a method of dipping a void-arranged structure in a solution in which an analyte is dissolved, washing a solvent and an excess analyte after sticking the analyte to the surface of the void-arranged structure, drying the void-arranged structure and thereafter measuring properties of the analyte with the aforementioned measuring apparatus can be cited, for example. Further, a method of sticking an analyte to a sheet-like substrate constituted of a polymer or the like, bringing a void-arranged structure into close contact with the sheet-like substrate and thereafter measuring properties of the analyte with the aforementioned measuring apparatus can be cited.

The void-arranged structure employed in the present invention, not particularly restricted so far as the same is a structure causing scattering when an electromagnetic wave is applied thereto, is preferably a quasi-periodic structure or a periodic structure. The quasi-periodic structure denotes a structure not having translational symmetry but keeping order in arrangement. As the quasi-periodic structure, a Fibonacci structure can be cited as a one-dimensional quasi-periodic structure, or a Penrose structure can be cited as a two-dimensional quasi-periodic structure, for example. The periodic structure denotes a structure having spatial symmetry represented by translational symmetry, and is classified into a one-dimensional periodic structure, a two-dimensional periodic structure and a three-dimensional periodic structure in response to the dimensions of the symmetry. As the one-dimensional periodic structure, a wire grid structure, a one-dimensional diffraction grating or the like can be cited, for example. As the two-dimensional periodic structure, a mesh filter, a two-dimensional diffraction grating or the like can be cited, for example. Among these periodic structures, the two-dimensional periodic structure is preferably employed. More specifically, a void-arranged structure or the like having void portions regularly arranged at least in one arrangement direction can be cited.

Figure 2:
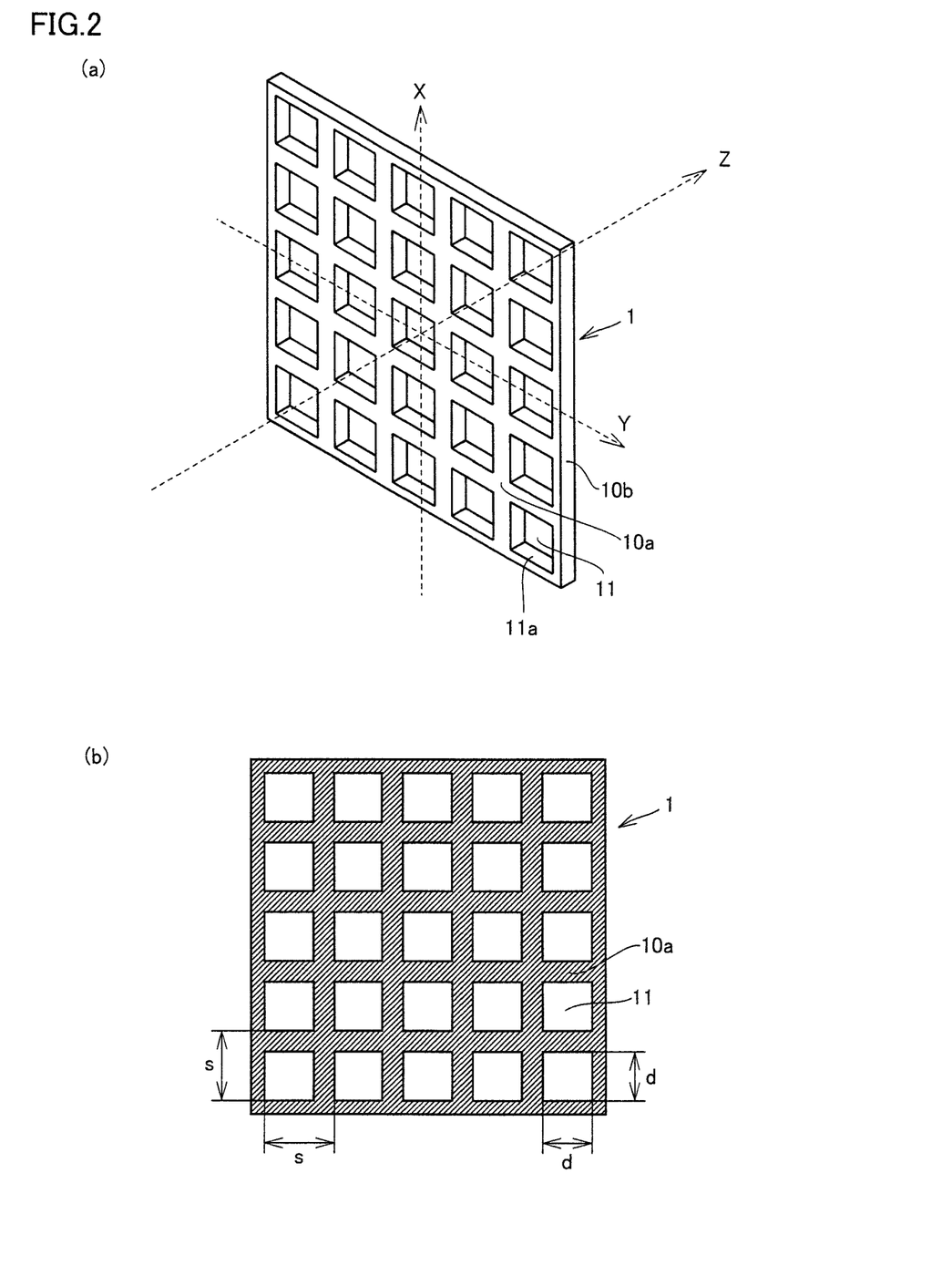
FIGS. 2(a) and 2(b) show schematic diagrams for illustrating a grating structure of a void-arranged structure (metal mesh filter) employed in the present invention.

As the two-dimensional periodic structure, a plate-like structure (grating-like structure) in which void portions are arranged at constant intervals in the form of a matrix as shown in FIGS. 2(a) and 2(b) can be cited, for example. Void-arranged structure 1 shown in FIG. 2(a) is a plate-like structure in which void portions 11 square as viewed from the side of a principal surface 10a thereof are provided at equal intervals in two arrangement directions (longitudinal and lateral directions in the figure) parallel to the respective sides of the squares.

While the dimensions and shapes of the void portions of the void-arranged structure are properly designed in response to the measurement method, material characteristics of the void-arranged structure, the frequency of a used electromagnetic wave and the like and it is difficult to generalize the ranges thereof, the grating space of the void portions denoted by $\underline{s}$ in FIG. 2(b) is preferably at least 1/10 of and not more than 10 times the wavelength of the electromagnetic wave employed for the measurement in void-arranged structure 1 shown in FIG. 2(a) in a case of detecting a forward-scattered electromagnetic wave. If the grating space $\underline{s}$ of the void portions is out of this range, scattering may be hard to cause. As a hole size of the void portions, the hole size of the void portions denoted by $\underline{d}$ in FIG. 2(b) is preferably at least 1/10 of and not more than 10 times the wavelength of the electromagnetic wave employed for the measurement. If the hole size of the void portions is out of this range, the strength of the transmitted (forward-scattered) electromagnetic wave may so weaken that it becomes difficult to detect a signal.

While the thickness of the void-arranged structure is properly designed in response to the measurement method, the material characteristics of the void-arranged structure, the frequency of the used electromagnetic wave and the like and it is difficult to generalize the range thereof, the same is preferably not more than several times the wavelength of the electromagnetic wave employed for the measurement in the case of detecting the forward-scattered electromagnetic wave. If the thickness of the structure becomes greater than this range, the strength of the forward-scattered electromagnetic wave may so weaken that it becomes difficult to detect the signal.

The void-arranged structure is preferably a structure causing a pseudo-TE11 mode resonance phenomenon by application of the electromagnetic wave in a case of regarding the individual void portions thereof as waveguides. The term of the pseudo-TE11 mode resonance phenomenon is employed in a sense of including a resonance phenomenon of a TE11 mode and a resonance phenomenon of a mode similar to the TE11 mode. The void-arranged structure is the structure causing the pseudo-TE11 mode resonance phenomenon, whereby there is such an advantage that a sharp dip waveform can be obtained.

The void-arranged structure is preferably a structure reducing a pseudo-TE10 mode resonance phenomenon by application of the electromagnetic wave in a case of regarding the individual void portions thereof as waveguides. In the structure reducing the pseudo-TE10 mode resonance phenomenon, the shape of the void portions is square, concave or trapezoidal. The shape is preferably concave or trapezoidal. The shape is more preferably trapezoidal. The term of the pseudo-TE10 mode resonance phenomenon is employed in a sense of including a resonance phenomenon of a TE10 mode and a resonance phenomenon of a mode similar to the TE10 mode. The void-arranged structure is the structure reducing the pseudo-TE10 mode resonance phenomenon, whereby there is such an advantage that a sharp dip waveform can be obtained.

In aforementioned measuring apparatus 2, properties of the analyte can be measured on the basis of that a dip waveform or the like caused in the frequency characteristic of the void-arranged structure changes due to the presence of the analyte.

Referring to FIG. 2(a), it is assumed that the lateral arrangement direction of void portions 11 is a Y-axis, and the longitudinal arrangement direction is an X-axis. It is also assumed that a direction perpendicular to the X-Y plane is a Z-axis. The traveling direction of the electromagnetic wave applied to void-arranged structure 1 is the Z-axis direction shown in FIG. 2(a), and the polarization direction of the electromagnetic wave is the X-axis direction shown in FIG. 2(a).

Any well-known method can be used as a method for holding the analyte on the void-arranged structure in the present invention, and the analyte may be directly stuck to the void-arranged structure, or may be stuck thereto through a support film or the like, for example. From a viewpoint of improving measuring sensitivity and performing measurement having high reproducibility by suppressing dispersion in measurement, the analyte is preferably directly stuck to the surface of the void-arranged structure.

As the case of directly sticking the analyte to the void-arranged structure, not only a case where chemical bonding or the like is directly formed between the surface of the void-arranged structure and the analyte, but also a case where, with respect to a void-arranged structure to whose surface host molecules have been previously bonded, the analyte is bonded to the host molecules is also included. Covalent bonding (covalent bonding between a metal and a thiol group, for example), van der Waals bonding, ionic bonding, metallic bonding, hydrogen bonding or the like can be cited as the chemical bonding, which is preferably the covalent bonding. The host molecules are molecules or the like capable of specifically bonding the analyte, and an antigen and an antibody, a sugar chain and protein, lipid and protein, a low-molecular compound (ligand) and protein, protein and protein, single-stranded DNA and single-stranded DNA or the like can be cited as a combination of the host molecules and the analyte, for example.

In the case of directly sticking the analyte to the void-arranged structure, a void-arranged structure in which at least a partial surface is formed by a conductor is preferably employed. At least a partial surface of void-arranged structure 1 is a partial surface of either one of principal surface 10a, a side surface 10b and a void portion side surface 11a shown in FIG. 2(a).

The conductor denotes an object (substance) conducting electricity, and not only a metal but also a semiconductor is included. As the metal, a metal capable of bonding to a functional group of a compound having the functional group such as a hydroxy group, a thiol group, a carboxyl group or the like, a metal whose surface can be coated with a functional group such as a hydroxy group, an amino group or the like, or an alloy of these metals can be cited. More specifically, gold, silver, copper, iron, nickel, chromium, silicon, germanium or the like can be cited, and the metal is preferably gold, silver, copper, nickel or chromium, and more preferably gold. In a case of employing gold or nickel and particularly in a case where the analyte has a thiol group (—SH group), it is advantageous since the thiol group can be bonded to the surface of the void-arranged structure. In a case of employing nickel and particularly in a case where the analyte has a hydroxy group (—OH) or a carboxyl group (—COOH), it is advantageous since the functional group can be bonded to the surface of the void-arranged structure. As the semiconductor, a compound semiconductor such as a group IV semiconductor (Si, Ge or the like), a group II-VI semiconductor (ZnSe, CdS, ZnO or the like), a group III-V semiconductor (GaAs, InP, GaN or the like), a group IV compound semiconductor (SiC, SiGe or the like) or a group I-III-VI semiconductor ($CuInSe_2$ or the like) or an organic semiconductor can be cited, for example.

As the case of sticking the analyte through the support film or the like, a method of pasting a support film of polyamide resin or the like to the surface of the void-arranged structure and sticking the analyte to the support film or a method of employing an airtight or liquid-tight container in place of the support film and measuring a fluid or a substance dispersed in a fluid can be specifically cited.

In the measurement method according to the present invention, properties of the analyte are measured on the basis of at least one parameter related to the frequency characteristic of the void-arranged structure obtained in the aforementioned manner. The present invention is characterized in that this parameter includes a quantity of change, resulting from the presence of the analyte, in the ratio of the detected electromagnetic wave to the applied electromagnetic wave at a specific frequency.

The aforementioned specific frequency is preferably a frequency other than the minimum point of the dip waveform in the frequency characteristic of the transmittance of the electromagnetic wave transmitted through the said void-arranged structure (1), or a frequency other than the maximum point of the peak waveform in the frequency characteristic of the reflectance of the electromagnetic wave reflected by the said void-arranged structure (1). Further, the aforementioned specific frequency is preferably on a higher frequency side or a lower frequency side than the minimum point of the aforementioned dip waveform or the maximum point of the peak waveform.

In addition, the aforementioned specific frequency is preferably a frequency excluding the minimum point in the dip waveform, or a frequency excluding the maximum point in the peak waveform.

The dip waveform is the waveform of a valley-shaped (downwardly convex) portion partially observed in the frequency characteristic (transmittance spectrum, for example) of the void-arranged structure in such a frequency range that the ratio (transmittance of the electromagnetic wave, for example) of the detected electromagnetic wave to the applied electromagnetic wave relatively enlarges. The peak waveform is a crest-shaped (upwardly convex) waveform partially observed in the frequency characteristic (reflectance spectrum, for example) of the void-arranged structure in such a frequency range that the ratio (reflectance of the electromagnetic wave, for example) of the detected electromagnetic wave to the applied electromagnetic wave relatively reduces.

In the present invention, the dip waveform denotes a waveform, including the minimum point of the aforementioned valley-shaped waveform, between maximum points on both sides of the minimum point. The peak waveform denotes a waveform, including the maximum point of the aforementioned crest-shaped waveform, between minimum points on both sides of the maximum point. For example, a dip waveform in a case where the frequency characteristic is a transmittance spectrum is a spectrum between frequencies $f_{peak1}$ and $f_{peak2}$ whose transmittance levels reach maximum values ($T_{peak1}$ and $T_{peak2}$) in front of and at the back of a peak frequency fx whose transmittance reaches the minimum value ($T_{dip}$), as shown in FIG. 3.

Figure 3:
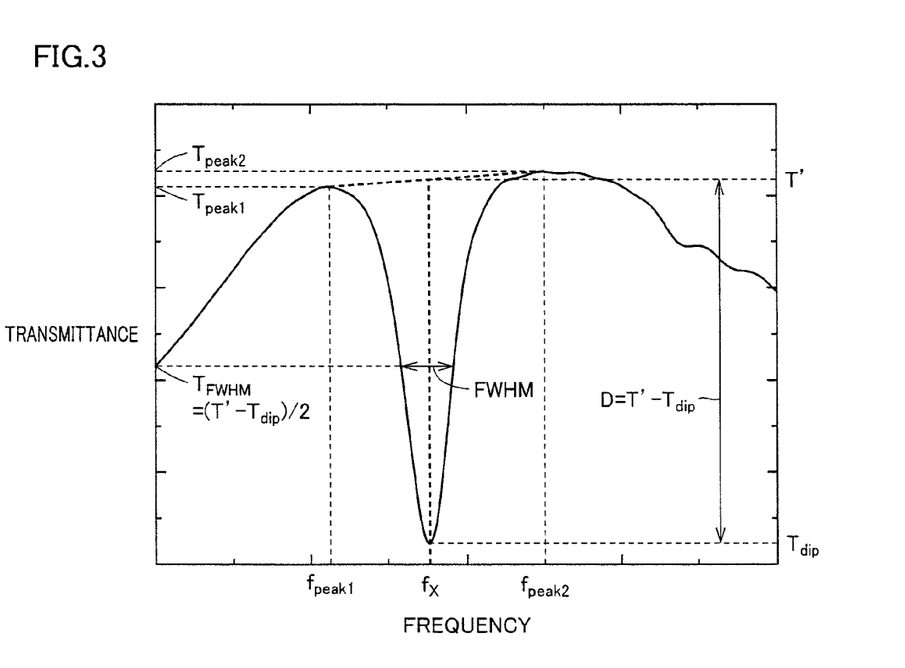
FIG. 3 is an explanatory diagram of respective variables of a transmittance spectrum defined in the present invention.

Referring to FIG. 3, it is assumed that $T_{peak1}$ represents transmittance (maximum value) at the frequency $f_{peak1}$ in a peak on a lower frequency side than a dip, $T_{peak2}$ represents transmittance (maximum value) at the frequency $f_{peak2}$ in a peak on a higher frequency side than the dip, and $T_{dip}$ represents transmittance (minimum value) at the frequency fx in a reverse peak of the dip. Further, it is assumed that T' represents the intersection point between a straight line coupling $T_{peak1}$ and $T_{peak2}$ with each other and fx, and an intermediate value $[T'+T_{dip})/2]$ of T' and $T_{dip}$ represents transmittance ($T_{FWHM}$) in a full width at half maximum (FWHM) of the dip waveform.

The aforementioned specific frequency is preferably a frequency outside a full width at half maximum (FWHM) in the aforementioned dip waveform or in the aforementioned peak waveform. In the case where the frequency characteristic is the transmittance spectrum, for example, the aforementioned specific frequency is preferably a frequency between the frequencies $f_{peak1}$ and $f_{peak2}$ excluding the frequency of the full width at half maximum (FWHM) shown in FIG. 3. This is because, in a case of measuring an analyte held on a void-arranged structure in a quantity of not more than about 100 $ng/mm^2$, the vicinity of the minimum point of a dip waveform of a transmittance spectrum or the like or the vicinity of the maximum point of a peak waveform of a reflectance spectrum or the like has such a tendency that the transmittance does not much change due to the presence of the analyte.

In a case where the aforementioned specific frequency is a frequency other than the aforementioned dip waveform or a frequency other than the aforementioned peak waveform, the ratio (transmittance or reflectance of the electromagnetic wave) of the detected electromagnetic wave to the applied electromagnetic wave at the aforementioned specific frequency is preferably a ratio in a frequency characteristic of a portion adjacent to the aforementioned dip waveform wherein the ratio of the detected electromagnetic wave to the applied electromagnetic wave is higher than that on both ends of a full width at half maximum (FWHM) of the dip waveform (portion upward beyond $T_{FWHM}$ on a lower frequency side of $f_{peak1}$ in FIG. 3 or a portion upward beyond $T_{FWHM}$ on a higher frequency side of $f_{peak2}$, for example), or in a frequency characteristic of a portion adjacent to the aforementioned peak waveform wherein the ratio of the detected electromagnetic wave to the applied electromagnetic wave is lower than that on both ends of a full width at half maximum (FWHM) of the peak waveform.

Depending on the type of the analyte or the shape of the void-arranged structure, the frequency of the electromagnetic wave at which the ratio (transmittance or reflectance) of the detected electromagnetic wave to the applied electromagnetic wave changes most in response to the quantity of the analyte of a small quantity may be a frequency out of the range of the dip waveform or the peak waveform. Also in this case, it is because the detection can be performed with higher sensitivity by employing the transmittance at the frequency in the constant range adjacent to the dip waveform or the peak waveform as the parameter than a case of employing transmittance at a frequency out of the range as the parameter.

The aforementioned parameter preferably includes a quantity of change, resulting from the presence of the analyte, in the width of the dip waveform or the peak waveform of the transmittance spectrum obtained when changing the frequency of the electromagnetic wave in the constant range. The width of the dip waveform or the peak waveform is difference in frequency of the dip waveform corresponding to specific transmittance with regard to the dip waveform in the transmittance spectrum, for example. More specifically, the full width at half maximum (width of the dip waveform in FWHM: $T_{FWHM}$ in FIG. 3) of the dip waveform in the transmittance spectrum shown in FIG. 3 or the like can be cited, for example.

In the method for measuring properties of an analyte by applying the electromagnetic wave to the void-arranged structure holding the analyte and analyzing the transmittance spectrum thereof, there is such a tendency that the change in the position (frequency) of the minimum value of the dip waveform or the maximum value of the peak waveform reduces and the detection becomes difficult as the quantity of the analyte reduces. In the measurement method according to the present invention, there is an effect of improving the measuring sensitivity (lowering the detection limit) by utilizing the measurement parameter other than the shifting in the position (frequency) of the minimum value of the dip waveform or the maximum value of the peak waveform.

In a case of employing only the quantity of change as to the ratio (transmittance or reflectance of the electromagnetic wave) of the detected electromagnetic wave to the applied electromagnetic wave at the specific frequency as the parameter, measurement of transmittance at continuous frequencies may not be performed every time but a mechanism or the like for acquiring frequency information is unnecessary for the apparatus employed for the measurement, whereby effects such as simplification and downsizing of a measuring mechanism, reduction of the measurement time and the like can be attained.

Also when employing a quantity of change, resulting from the presence of the analyte, in electromagnetic wave transmittance at one specific frequency as the parameter, it may be possible to measure properties of the analyte with higher sensitivity by combining quantities of change, resulting from the presence of the analyte, in electromagnetic wave transmittance levels at a plurality of specific frequencies as measurement parameters. As parameters combined in this manner, not only the aforementioned quantity of change, resulting from the presence of the analyte, in the transmittance of the electromagnetic wave at each frequency and the quantity of change, resulting from the presence of the analyte, in the width of the dip waveform or the peak waveform, but also the quantity of change, resulting from the presence of the analyte, in the frequency of the minimum point of the dip waveform or the maximum point of the peak waveform may be combined.

EXAMPLES

While the present invention is now described in more detail with reference to Examples, the present invention is not restricted to these.

Example 1

In this Example, a metal mesh filter (hereinafter abbreviated as MMF), having tetragonally latticed square holes shown in the schematic diagrams of FIGS. 2(a) and 2(b), made of Ni as a whole was used as a void-arranged structure. The grating space (s in FIG. 2(b)), the hole size (d in FIG. 2(b)) and the thickness of this MMF were 260 μm, 180 μm and 20 μm respectively, and the shape of the whole was a discoidal shape of 14 mm in diameter. This MMF is a structure causing a pseudo-TE11 mode resonance phenomenon. Measurement employing bovine serum albumin as an analyte was performed by employing such an MMF.

First, 0.1 weight % of an aqueous bovine serum albumin solution was directly applied to the surface of the MMF with an ink jet printer. The quantity of the aqueous bovine serum albumin solution applied onto the MMF was controlled in the range of 675 pg/mm$^2$ to 1688 pg/mm$^2$ by discharging droplets of one shot (=14 pL) per 35.5 μm square and wet-on-wet-applying the aqueous solution while controlling the shot number. This MMF coated with the aqueous bovine serum albumin solution was naturally dried one night in a desiccator.

Figure 4:
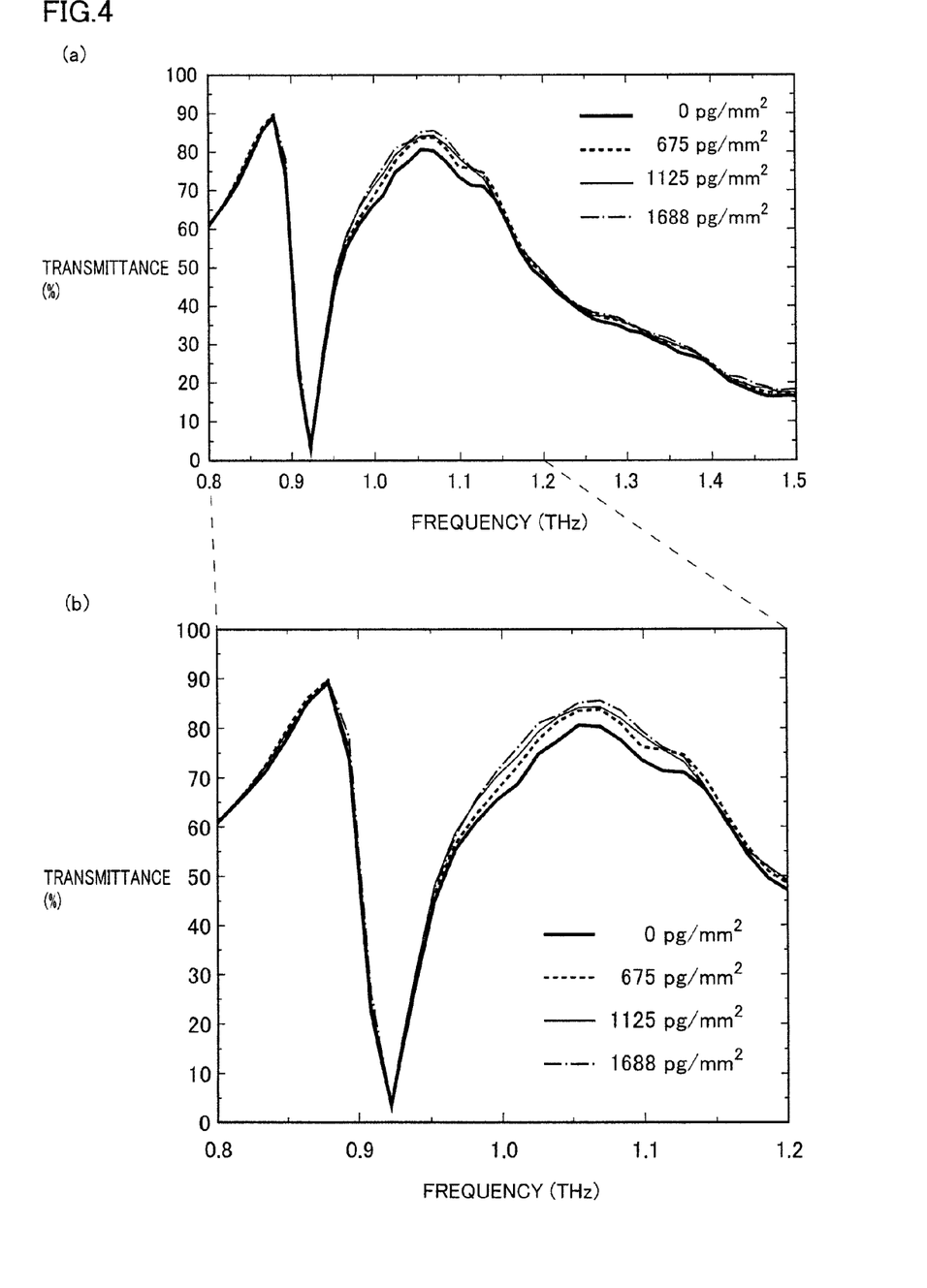
FIG. 4(a) is a graph showing transmittance spectra of Example 1.
FIG. 4(b) is a partially enlarged view of FIG. 4(a).

After confirming that the MMF surface had been dried, a transmittance spectrum of the MMF coated with the bovine serum albumin was measured by employing terahertz time domain spectroscopy (THz-TDS). Frequency resolution was measured at 15 GHz as to each sample. As a control, an MMF was similarly prepared and subjected to measurement also as to an MMF (quantity of application of bovine serum albumin: 0 ng/mm$^2$) coated with pure water in place of the aqueous bovine serum albumin solution. FIG. 4 show average transmittance spectra at a time of performing measurement five times as to the MMF coated with each quantity of bovine serum albumin (FIG. 4(b) is an enlarged view around dip waveforms of FIG. 4(a)).

With regard to the shapes of the transmittance spectra shown in FIGS. 4(a) and 4(b), frequencies (fx) of reverse peaks of dip waveforms do not change at all when the quantities of albumin are small quantities of not more than about several ng/mm$^2$. However, change is observed in the magnitudes of the transmittance levels in transmittance spectra mainly at frequencies of at least about 0.95 THz. Such a tendency that the change in the spectra is proportional to change in the quantities of albumin in the vicinity of the frequency of 1.0 THz is observed from the enlarged view of FIG. 4(b).

Figure 5:
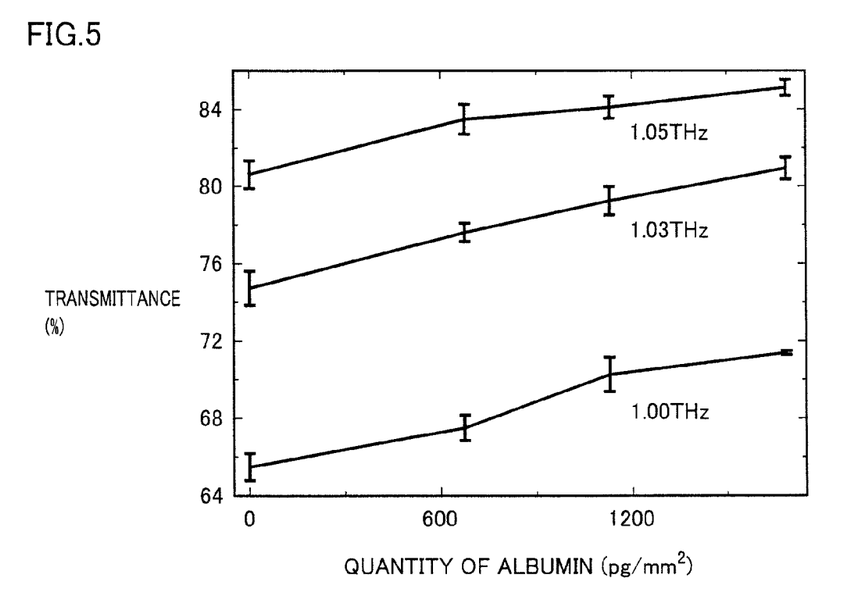
FIG. 5 is a graph plotting transmittance levels of electromagnetic waves having frequencies of 1.00 THz, 1.03 THz and 1.05 THz in the transmittance spectra of FIG. 4 with respect to quantities of albumin.

With respect to the results of FIGS. 4(a) and 4(b), transmittance levels at the respective frequencies of 0.8 THz to 1.2 THz were plotted with respect to the quantities of samples (quantities of albumin), to examine whether or not the quantities of analytes had been detectable. As a result, it has been recognized that the quantities of the analytes had been partially detectable in the frequency domain of 0.98 THz to 1.08 THz. FIG. 5 is a graph plotting electromagnetic wave transmittance levels at the frequencies of 1.00 THz, 1.03 THz and 1.05 THz in the transmittance spectra of FIG. 4 with respect to the quantities of albumin. As shown in FIG. 5, it is understood that the transmittance levels at the frequency of 1.03 THz have higher correlativeness with the quantities of albumin than the transmittance levels at the frequencies of 1.00 THz and 1.05 THz and had been entirely detectable in isolation from 0 pg/mm$^2$ up to 1688 pg/mm$^2$ with no overlapping of error bars.

Example 2

Modeled on the following void-arranged structure, simulations of reflectance were conducted by employing an electromagnetic field simulator MicroStripes (registered trademark) by CST Japan K.K.

In this Example, the void-arranged structure employed as the model is a plate-like structure, having tetragonally latticed square holes shown in the schematic diagram of FIG. 2(a), made of copper as a whole. The grating space (s shown in FIG. 2(b)), the hole size (d shown in FIG. 2(b)) and the thickness of this void-arranged structure are 260 μm, 180 μm and 60 μm respectively, and the shape of the whole is a plate-like body of 1.3 mm square.

Figure 6:
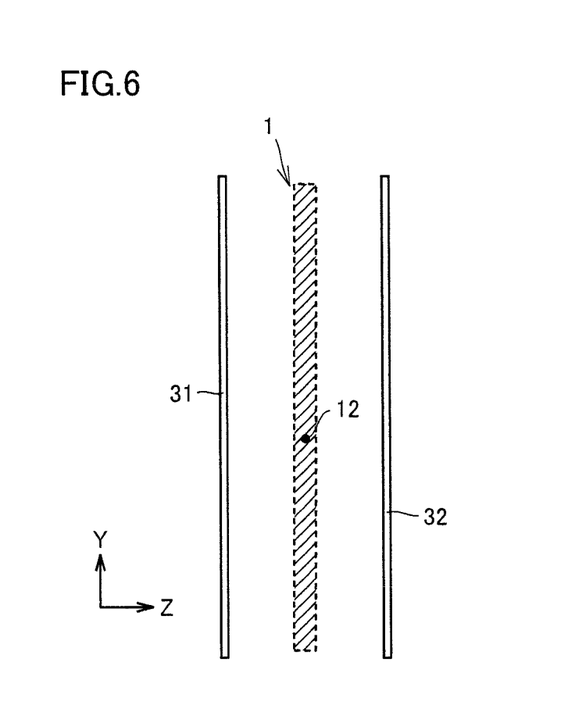
FIG. 6 is a schematic sectional view for illustrating arrangement of a void-arranged structure and the like assumed in a simulation of Example 2.

Simulations as to a model in which such a void-arranged structure was set between two ports 31 and 32 arranged at an interval of 460 μm as shown in FIG. 6 were conducted. The distance between port 31 and the center 12 of gravity of the void-arranged structure is 230 μm. The distance between port 32 and the center of gravity of the void-arranged structure is 230 μm. Port 31 is a plate-like body of 10 μm in thickness having a principal surface of 1.3 mm square, and serves also as a light source and a measuring member for the quantity of light reflected by the void-arranged structure. Port 32 is a plate-like body of 10 μm in thickness having a principal surface of 1.3 mm square, and a measuring member for the quantity of light transmitted through the void-arranged structure. Simulations were conducted as to a case where dielectric substances (∈r=2.4) uniformly adhered to inner sides of holes with a thickness of 1.5 μm and a case where nothing adhered thereto.

Figure 7:
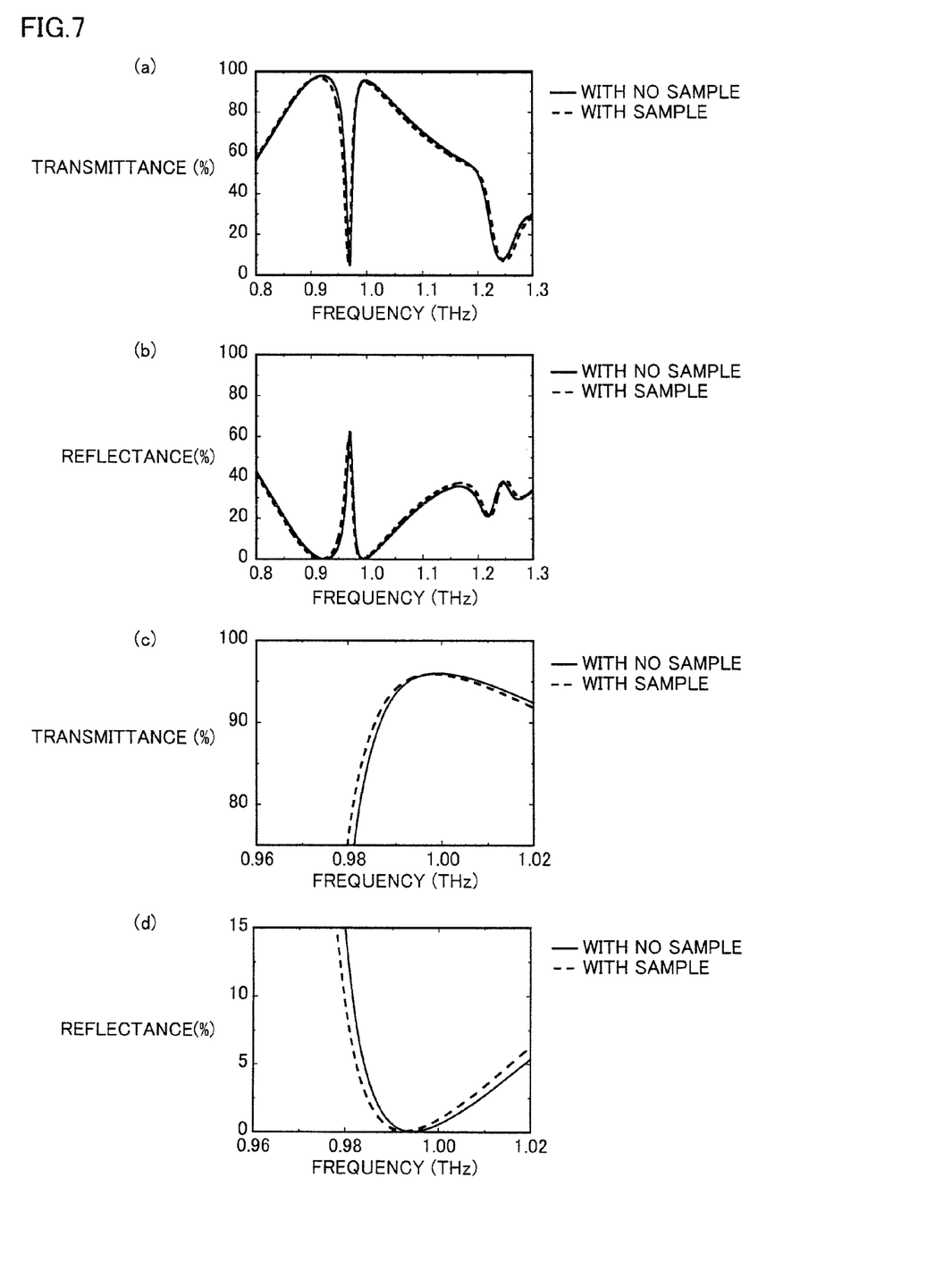
FIG. 7(a) shows transmittance spectra obtained by simulation calculations in Example 2.
FIG. 7(b) shows reflectance spectra obtained by simulation calculations in Example 2.
FIG. 7(c) shows an enlarged view around maximum points of dip waveforms of FIG. 7(a).
FIG. 7(d) shows an enlarged view around minimum points of peak waveforms of FIG. 7(b).

FIGS. 7(a) and 7(b) show transmittance spectra and reflectance spectra obtained by calculations respectively. FIGS. 7(c) and 7(d) show enlarged diagrams in the vicinity of maximum points of dip waveforms of FIG. 7(a) and in the vicinity of minimum points of peak waveforms of FIG. 7(b) respectively. As to the transmittance spectra and the reflectance spectra shown in FIGS. 7(c) and 7(d), it is understood that the transmittance levels in the vicinity of the maximum points of the dip waveforms in the transmittance spectra and the reflectance levels in the vicinity of the minimum points of the peak waveforms in the reflectance spectra change due to the adhesion of the dielectric substances.

The embodiment and Examples disclosed this time must be considered as illustrative in all points and not restrictive. The range of the present invention is shown not by the above description but by the scope of claims for patent, and it is intended that all modifications within the meaning and range equivalent to the scope of claims for patent are included.

REFERENCE SIGNS LIST 1 void-arranged structure, 10a principal surface, 10b side surface, 11 void portion, 11a void portion side surface, 12 center of gravity, 2 measuring apparatus, 21 application portion, 22 detection portion, 23 application control portion, 24 analytical treatment portion, 25 display portion, 31, 32 port.

The invention claimed is:
1. A measurement method comprising:
applying an electromagnetic wave to a void-arranged structure holding an analyte; and
detecting a scattered electromagnetic wave from said void-arranged structure to enable measuring of properties of said analyte based on at least one parameter, wherein
said at least one parameter includes a quantity of change in a ratio of the scattered electromagnetic wave to the applied electromagnetic wave at a specific frequency,
wherein said specific frequency is a frequency other than a minimum point of a dip waveform in a frequency characteristic of transmittance of the scattered electromagnetic wave or a frequency other than a maximum point of a peak waveform in a frequency characteristic of reflectance of the scattered electromagnetic wave.

2. The measurement method according to claim 1, wherein said frequency is on a higher frequency side or a lower frequency side relative to the minimum point of said dip waveform or said frequency is on a higher frequency side or a lower frequency side relative to the maximum point of said peak waveform.

3. The measurement method according to claim 2, wherein said frequency is in said dip waveform or in said peak waveform.

4. The measurement method according to claim 3, wherein said frequency is outside a full width at half maximum in said dip waveform or said frequency is outside a full width at half maximum in said peak waveform.

5. The measurement method according to claim 4, wherein the ratio of the scattered electromagnetic wave to the applied electromagnetic wave is in a frequency characteristic of a portion adjacent to said dip waveform wherein the ratio of the scattered electromagnetic wave to the applied electromagnetic wave is higher than that of both ends of the full width at half maximum of the dip waveform, or
the ratio of the scattered electromagnetic wave to the applied electromagnetic wave is in a frequency characteristic of a portion adjacent to said peak waveform wherein the ratio of the scattered electromagnetic wave to the applied electromagnetic wave is lower than that of both ends of the full width at half maximum of the peak waveform.

6. The measurement method according to claim 1, wherein said parameter includes a quantity of change in a width of a dip waveform or a quantity of change in a width of a peak waveform.

7. The measurement method according to claim 1, wherein said void-arranged structure is configured to cause pseudo-TE11 mode resonance phenomenon.

8. The measurement method according to claim 1, wherein said void-arranged structure is configured to reduce a pseudo-TE10 mode resonance phenomenon.

* * * * *